US009747722B2

(12) United States Patent
Adler et al.

(10) Patent No.: US 9,747,722 B2
(45) Date of Patent: Aug. 29, 2017

(54) METHODS FOR TEACHING AND INSTRUCTING IN A VIRTUAL WORLD INCLUDING MULTIPLE VIEWS

(71) Applicant: REFLEXION HEALTH, INC., San Diego, CA (US)

(72) Inventors: Martin Adler, San Diego, CA (US); Ravi Komatireddy, San Diego, CA (US); Richard Hicks, III, San Diego, CA (US); Joseph Mares, Irvine, CA (US); Spencer Hutchins, San Diego, CA (US)

(73) Assignee: REFLEXION HEALTH, INC., San Diego, CA (US)

( * ) Notice: Subject to any disclaimer, the term of this patent is extended or adjusted under 35 U.S.C. 154(b) by 0 days.

(21) Appl. No.: 14/667,985

(22) Filed: Mar. 25, 2015

(65) Prior Publication Data

US 2015/0339854 A1  Nov. 26, 2015

Related U.S. Application Data

(60) Provisional application No. 61/970,609, filed on Mar. 26, 2014.

(51) Int. Cl.
*G06T 19/00* (2011.01)
*G06K 9/00* (2006.01)
(Continued)

(52) U.S. Cl.
CPC .......... *G06T 19/003* (2013.01); *A63F 13/213* (2014.09); *A63F 13/55* (2014.09);
(Continued)

(58) Field of Classification Search
CPC .............. G06F 3/011; G06F 2203/012; G06F 3/04815; G06F 17/5009; G06F 3/012;
(Continued)

(56) References Cited

U.S. PATENT DOCUMENTS 6,056,671 A   5/2000  Marmer
6,685,480 B2  2/2004  Nishimoto et al.
(Continued)

OTHER PUBLICATIONS

Patel, Kayur, et al. "The effects of fully immersive virtual reality on the learning of physical tasks." Proceedings of the 9th Annual International Workshop on Presence, Ohio, USA. 2006.*
(Continued)

*Primary Examiner* — Sultana M Zalalee
(74) *Attorney, Agent, or Firm* — David B. Murphy; O'Melveny & Myers LLP

(57) ABSTRACT

Methods, systems and apparatus are provided for generating visual instruction to a user of a system, such as for exercise instruction or rehabilitation purposes. Preferably, the system includes a user imaging system with the system generating an output adapted to couple to a display device. The systems and methods serve to guide a user body motion. In one preferred embodiment, the method includes the steps of receiving first user positional information from the user imaging system, and then generating a first mirror image of the user positional information. Additionally, the method includes generating a first instructional image having the same positional orientation as the first mirror image of the user positional information. Finally, the method and system generate a composite output display including the first mirror image of the user positional information and the first instructional image.

20 Claims, 5 Drawing Sheets

(51) Int. Cl.
*G06T 13/40* (2011.01)
*H04N 13/00* (2006.01)
*H04N 13/02* (2006.01)
*G09B 19/00* (2006.01)
*A63F 13/655* (2014.01)
*A63F 13/213* (2014.01)
*A63F 13/55* (2014.01)
*G06F 19/00* (2011.01)

(52) U.S. Cl.
CPC ........ *A63F 13/655* (2014.09); *G06F 19/3481* (2013.01); *G06K 9/00342* (2013.01); *G06T 13/40* (2013.01); *G06T 19/006* (2013.01); *G09B 19/003* (2013.01); *H04N 13/004* (2013.01); *H04N 13/0275* (2013.01); *G06T 2200/04* (2013.01); *G06T 2200/24* (2013.01); *G06T 2207/10016* (2013.01); *G06T 2207/10024* (2013.01); *G06T 2207/10028* (2013.01); *G06T 2207/30196* (2013.01); *G06T 2207/30221* (2013.01); *G06T 2213/08* (2013.01); *G06T 2219/004* (2013.01); *G06T 2219/2016* (2013.01)

(58) Field of Classification Search
CPC ........ G06F 3/017; G06F 3/013; G06F 3/0346; G06F 3/04842; A63F 13/428; A63F 2300/69; A63F 13/5375; A63F 2300/305; A63F 2300/6607; A61B 5/1114; A61B 5/1128; A61B 2505/09; A61B 5/1116; A63B 2024/0096; A63B 24/0003; G06K 9/00342; G06T 19/006; G02B 27/0093; G09B 9/00
See application file for complete search history.

(56) References Cited

U.S. PATENT DOCUMENTS

| | | | |
|---|---|---|---|
| 7,308,112 | B2 | 12/2007 | Fujimura et al. |
| 7,433,024 | B2 | 10/2008 | Garcia et al. |
| 8,306,635 | B2 | 11/2012 | Pryor |
| 8,322,856 | B2 | 12/2012 | Vertegaal et al. |
| 8,405,706 | B2 | 3/2013 | Zhang et al. |
| 8,535,130 | B2 | 9/2013 | Ciarrocchi |
| 8,608,480 | B2 | 12/2013 | Chan et al. |
| 8,926,330 | B2 | 1/2015 | Taghavi |
| 2005/0181347 | A1 | 8/2005 | Barnes et al. |
| 2006/0281977 | A1 | 12/2006 | Soppet |
| 2008/0191864 | A1 | 8/2008 | Wolfson |
| 2009/0176581 | A1 | 7/2009 | Barnes et al. |
| 2009/0252423 | A1 | 10/2009 | Zhu et al. |
| 2009/0318775 | A1 | 12/2009 | Michelson et al. |
| 2010/0022351 | A1 | 1/2010 | Lanfermann et al. |
| 2010/0190610 | A1 | 7/2010 | Pryor et al. |
| 2010/0199228 | A1 | 8/2010 | Latta et al. |
| 2011/0054870 | A1 | 3/2011 | Dariush et al. |
| 2011/0098109 | A1 | 4/2011 | Leake et al. |
| 2012/0021833 | A1 | 1/2012 | Boch et al. |
| 2012/0182431 | A1 | 7/2012 | Asanov |
| 2012/0206577 | A1 | 8/2012 | Guckenberger et al. |
| 2013/0055112 | A1* | 2/2013 | Joseph ................ G06Q 10/107 715/758 |
| 2013/0123667 | A1 | 5/2013 | Komatireddy et al. |
| 2014/0370470 | A1 | 12/2014 | Aristizabal et al. |

OTHER PUBLICATIONS

Anderson, et al, "Lean on Wii: Physical Rehabilitation With Virtual realty and Wii Peripherals", Annual Review of Cybertherapy and Telemedicine 2010, IOS Press, 2010, ISBN: 1607505606, pp. 229-234.
Chen, et al., "Networking Telemedicine in Portable Rehabilitation Robot Monitor System", Journal of Applied Information Technology, vol. 3, No. 1, 2007, 7 pages.
Cook, "Microsoft Picks 11 Startups for new Kinect Accelerator", http://www.geekwire.com/2012/Microsoft-names-11-startups-kinect-accelarator /, Apr. 2, 2012. 6 pages.
Lakeside Center for Autism, "Technology", http:///www.lakesideautism.com/technology/2012, 3 pages.
Lakeside Center for Autism, "Kinetix Academy Begins!", http://www.lakesideautism.com/2012/05/20/kinetix-academy-begins/, May 20, 2012, 6 pages.
Lakeside Center for Autism, "We Did It!", http://www.lakesideautism.com/2012/05/21/we-did-it/, May 21, 2012, 4 pages.
Nosowitz, "Using the Microsoft Kinect to Detect Autism", www.popsci.com/technology/article/2012-05/using-microsoft-kinect-detect-autism, May 8, 2012, 3 pages.
Toppo, "Video Games Help Autistic Students in Classrooms", http://www.usatoday.com/news/health/story/2012-05-31/video-games-autism-students/55319452/1, Jun. 1, 2012, 4 pages.
Woodward, "Microsoft's Kinect Accelerator: The Real Scoop on the Lucky Few", http://wwwxeconomy.com/seattle/2012/04/02/microsoft-kinect-accelerator-teams/ , Apr. 2, 2012, 5 pages.
Young, "Motion Sensors in Physical Therapy", Norwegian University of Science and Technology Department of Computer and Information Science, Dec. 2010, 108 pages.
International Search Report for PCT/US2015/022504, dated Jun. 25, 2015.

\* cited by examiner

METHODS FOR TEACHING AND INSTRUCTING IN A VIRTUAL WORLD INCLUDING MULTIPLE VIEWS

PRIORITY CLAIM

This application claims priority to and the benefit of U.S. Provisional Application No. 61/970,609, filed Mar. 26, 2014, entitled "Systems And Methods For Teaching And Instructing In A Virtual World Including Multiple Views" (our Ref. 701,376-001), which is hereby expressly incorporated herein by reference in its entirety as if fully set forth herein.

FIELD OF THE INVENTION

Systems and methods are provided to generate display images to a user of the methods and systems for teaching and instructing in a virtual world. More particularly, they relate to the use of multiple views in the display images.

BACKGROUND OF THE INVENTION

Virtual worlds, those that recreate or represent real three dimensional (3D) space can be used as environments to demonstrate, coach, and guide user body motion for the purposes of exercise and rehabilitation instruction. These digital environments can employ the use of an animated character, or avatar, in addition to other on-screen feedback to provide real time instruction and visual representation of motion. This motion specifically refers to limb or body motion. Using various camera technologies, including both RGB and depth cameras, a second 'user' animation can be placed into the virtual 3D environment to provide side by side, preferably real time, representation of real user limb and body motion, including physical orientation to the camera, real world surroundings, and location within the virtual environment (including perceived interaction with virtual elements).

Systems that employ virtual worlds that present motion instruction exhibit a common problem, namely it is difficult for the user to understand how their movement in the "real" world links to their digital representation (e.g. avatar, character, animation, etc.) in the "virtual" world. In particular, there can be difficulty determining which limb characters in a virtual world are using. In many applications (such as video games), products resolve this by "mirroring" the avatar (in the virtual world) with the player (in the real world). So when the player moves their left arm, for example, the avatar will move their right, similar to the effect observed when individuals move while watching their reflection in front of a mirror.

However, for more complex and/or clinically specific motions, this can be confusing for several reasons. First, if people are unfamiliar with game conventions, they can notice that the avatar is instructing them to move the "wrong" limb, that is, if the instruction is intended to have the user raise their right arm, the user raises their left arm as a result of the instructional avatar using their left arm. Second, the patient may need to see multiple angles of the digital avatar/coach to understand the motion properly. Third, for experiences using motion-tracking cameras (e.g. the Microsoft Kinect), the user may have to stand orthogonal (at an angle) to the camera so that their relevant limbs can be properly tracked. In those circumstances, the confusion can be greatly exacerbated.

The systems and methods described herein provide a novel solution to these problems.

SUMMARY OF THE INVENTION

Methods and apparatus are provided for generating visual instruction to a user of a system. Preferably, the system includes a user imaging system with the system generating an output adapted to couple to a display device. The systems and methods serve to guide a user body motion, such as for exercise instruction or rehabilitation purposes. In one preferred embodiment, the method includes the steps of receiving first user positional information from the user imaging system, and then generating a first mirror image of the user positional information. Additionally, the method includes generating a first instructional image having the same positional orientation as the first mirror image of the user positional information. Finally, the method and system generate a composite output display including the first mirror image of the user positional information and the first instructional image.

In yet another aspect of the inventions, the method additionally includes a second instructional image in a mirror image orientation to the first instructional image. By way of example, this second image could comprise a view of the back of the instructor whose front is depicted in the first instructional image. In this way, the display may optionally include an image of the user, as well as both a front and back display for the instructional image.

The major components of this innovation are as follows. First, it provides synchronous multi-view animation that show more than one point of view of the instructed motion in the virtual world. Second, it provides the use of a virtual animated 'mirror' that displays the additional angles of view and other feedback of the animated avatar. Third, it provides representation of both the guiding animation and synchronized patient avatar within the confines of the virtual mirror element. Fourth, it provides for dynamic state change of the mirror element as needed depending upon the context of the instruction e.g. obscuration of the reflection, zoom in and out, other image manipulation.

DETAILED DESCRIPTION OF THE INVENTION

Figure 1:
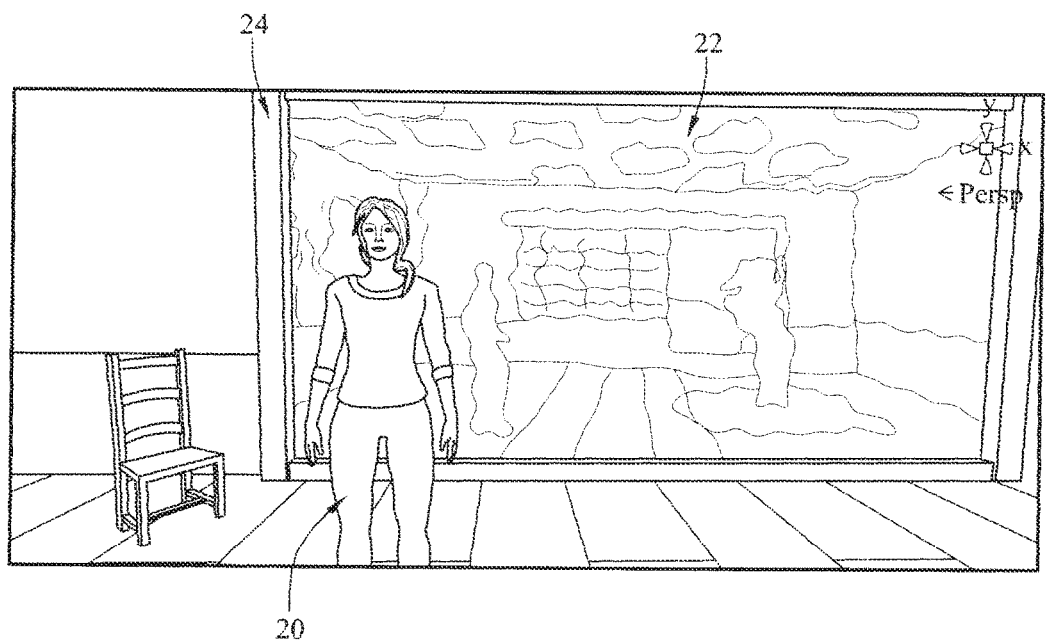
FIG. 1 shows a display with a coach avatar in the foreground and the mirror portion obscured.

FIG. 1 shows a display with a coach avatar 20 in the foreground and the mirror portion 22 obscured. The mirror portion is shown bounded by a frame 24 as an optional aid for the user to appreciate that the image shown in the mirror portion 22 is rendered as a mirror image of another object (e.g., the instructor and/or the user). This view minimizes environmental distraction and focuses the patient on the information being conveyed by the exercise coach. The terms instructor or coach are used interchangeably, and refer to the image intending to display the desired action or position to the user of the system. This view is used when important information is being conveyed to the patient prior to, in between or post exercise session. This view can be 'zoomed' in to put more focus on the coach's face as she is talking to the patient. Note that the mirror treatment may vary. For example, the mirror portion is here shown in an extreme matte format so as to avoid providing 'reflected' information that is distracting or not necessary or useful for the user.

Figure 2A:
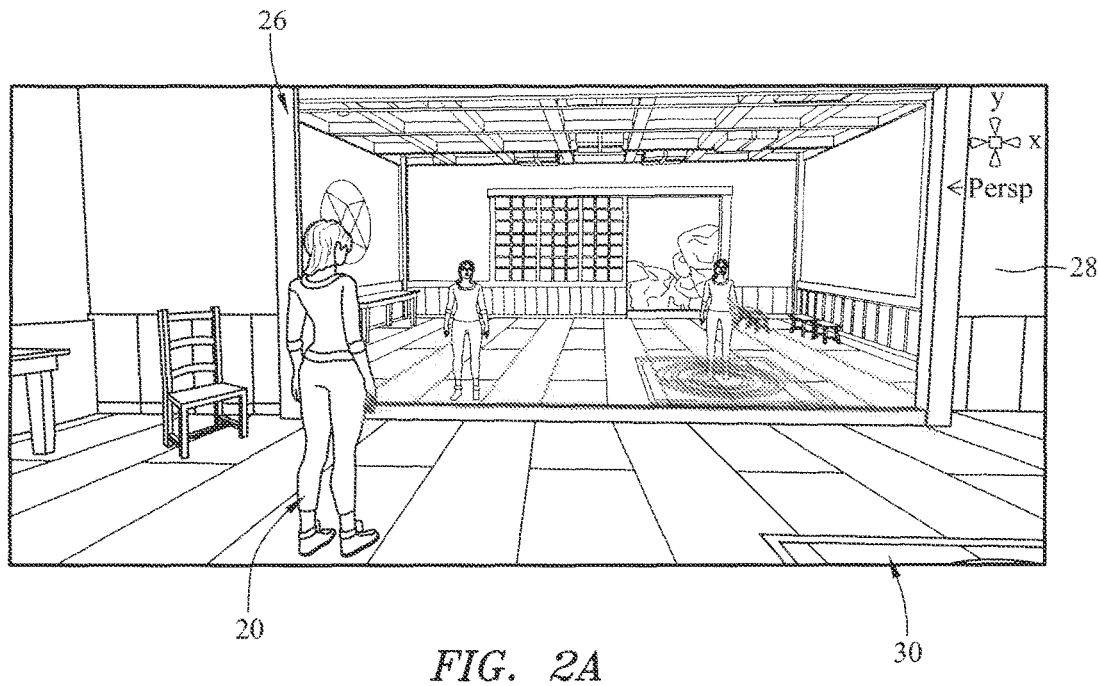
FIG. 2A shows a display with the coach avatar in the foreground, and the patient and coach avatar in the mirror.

FIG. 2A shows a display with the coach avatar 20 in the foreground, left had side of the display, and the patient and coach avatar in the mirror region 22. This view helps to demonstrate to the patient the proper technique to safely perform a clinician prescribed exercise. The position and actions of the instructional avatar depict the backside of the instructional avatar in the foreground, and the frontside of the instructional avatar in the mirrored display portion 22 of the display. This view is primarily used for instructing exercises and during the initial repetitions of a patient exercising. Currently, when depth cameras render persons on a screen, the individual is displayed in a mirrored version of themselves 28 and are displayed in the mirrored section 22 of the display. By placing the coach avatar in the foreground and both the patient and coach avatar in the 'mirror', the system shows the patient the proper body areas to move (ex. arm or leg) as it relates to their actual perspective in the 'real world'.

Figure 2B:
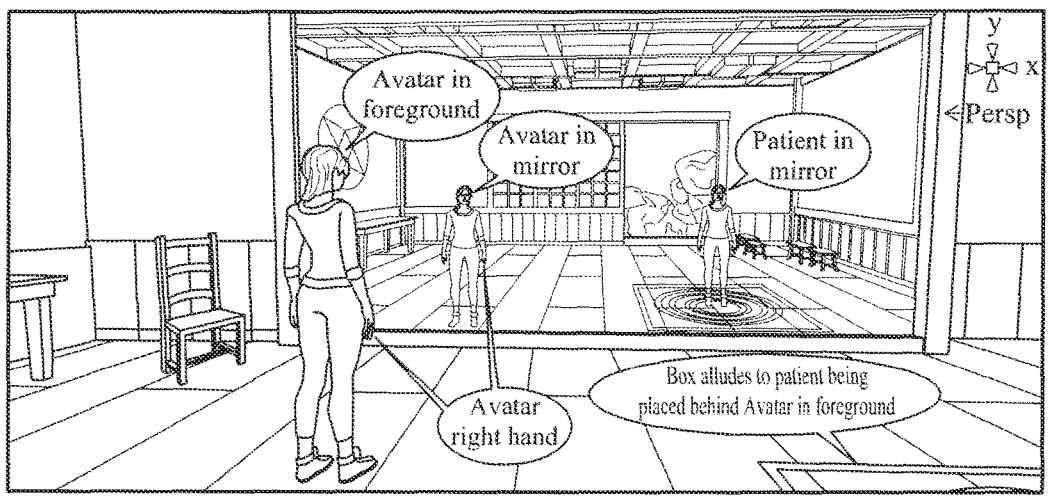
FIG. 2B shows the image of FIG. 2 but including annotations.

FIG. 2B shows the image of FIG. 2 but including annotations. Note the connection to the coach avatar's 'right hand' as it would be in 'reality' (on the right of the body) and as it appears 'mirrored' in the mirror (on the left side of the body). This view helps the patient to understand that mirroring is occurring and helps to visually inform them that they should sync their movements with the avatar in the foreground such that they appear perfectly synced in the mirror. The annotations include specific identification of the avatar, identifying the 'avatar in foreground', 'avatar in mirror', and identify the corresponding had of the avatar ('avatar right hand'). A rendering 28 of the user or patient (the terms are used interchangeably herein). As shown, the user positional information is used to generate a mirror image of the user, and then to provide a rendering 28 within the mirrored portions 22 of the display. The system compares the user positional information with the desired position and/or action as shown in the first instructional image. For example, if the user performs an action exactly as shown by the instructional image, the instructional image and the user positional images would show similarity of actions and positions. However, if the user does not accurately emulate the instructional image, the differences between the desired instructional image position and/or action may be displayed to the user. For example, if the instructional image is to perform a squat exercise, if the user does not move low enough as determined by comparison of the user positional information with the action deemed in sufficient compliance by the system, then the user will be instructed that their action does not qualify to count as a rep (repeat unit) of the exercise. Optionally an overlay image 30, such as a box, may be used both in the foreground and then mirror image 22 as an aid to the user to identify the user position in space and on the display.

Figure 3A:
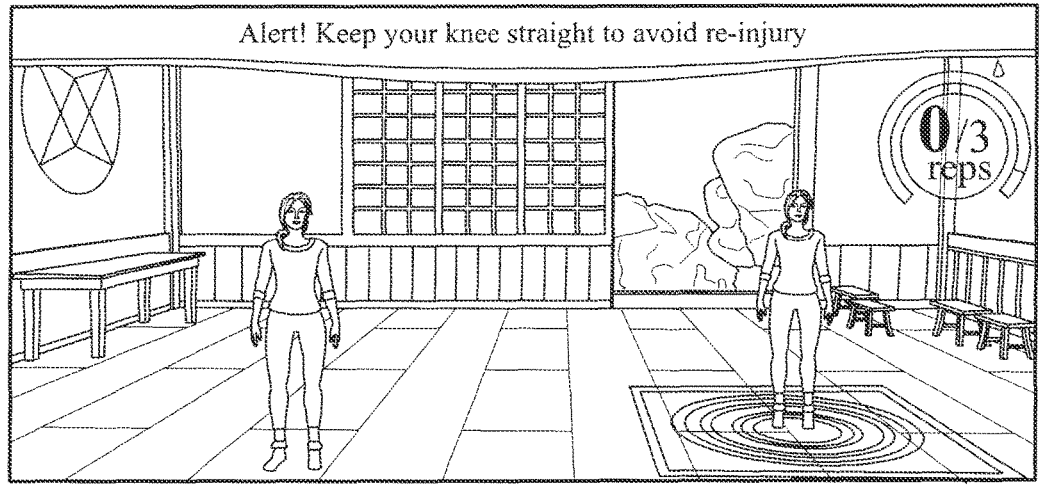
FIG. 3A shows a display with a coach avatar, but with the patient image in a mirrored orientation.

FIG. 3A shows a display with a coach avatar 20, but with the patient image 28 in a mirrored orientation. This state of the application is used once the patient has demonstrated competence in the exercise movement as it was instructed and initiated in state of FIG. 2 (see above). Again, if the user positional information corresponds to the position or range of positions or actions that are deemed compliant by the system, then the user is optionally advised of the number of reps completed. As shown in FIG. 3, "0/3" or zero of the three required reps have been performed.

Figure 3B:
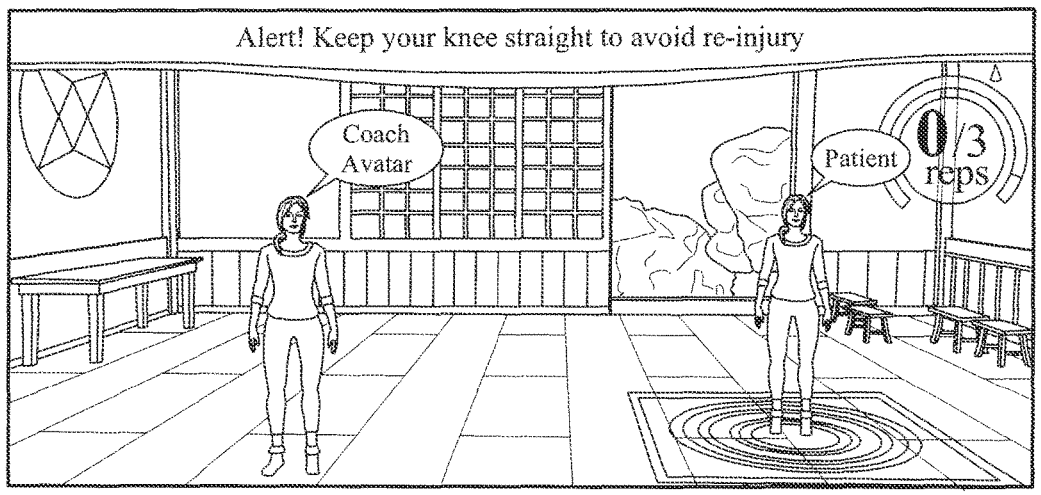
FIG. 3B shows the display image of FIG. 3 but including annotations.

FIG. 3B shows the display image of FIG. 3 but including annotations. The images have labeled as the 'coach avatar' 20 and 'patient' or user 28. As shown in this figure, the patient has been represented as an avatar identical to the coach avatar. The patient 'look' may be in any form known to those skilled in the art, ranging from photo realistic of the user, to an abstracted image, or avatar or cartoon image or the user, or of any arbitrary image, avatar or cartoon.

Figure 4:
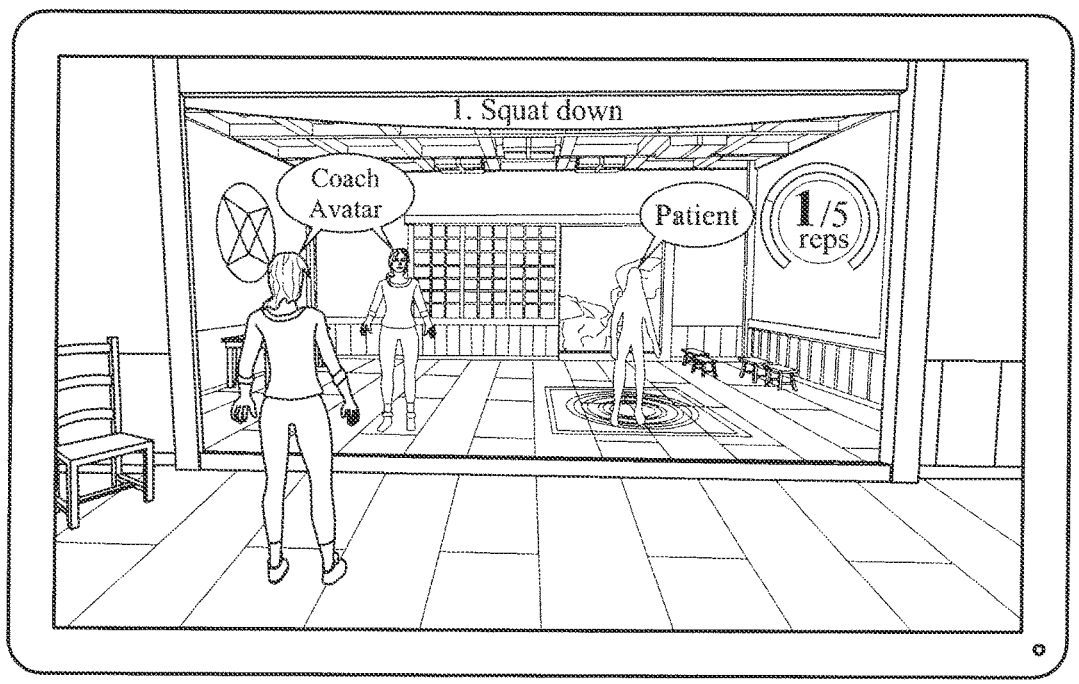
FIG. 4 shows a display unit showing a display image of a mirror version of the user's positional information, as well as both a first instructional image having the same positional orientation as the first mirror image and a second instructional image in a mirror image orientation to the first instructional image.

FIG. 4 shows a display unit 10 showing a display image of a mirror version of the user's positional information (as shown in FIG. 4), as well as both a first instructional image having the same positional orientation as the first mirror image and a second instructional image in a mirror image orientation to the first instructional image.

Figure 5:
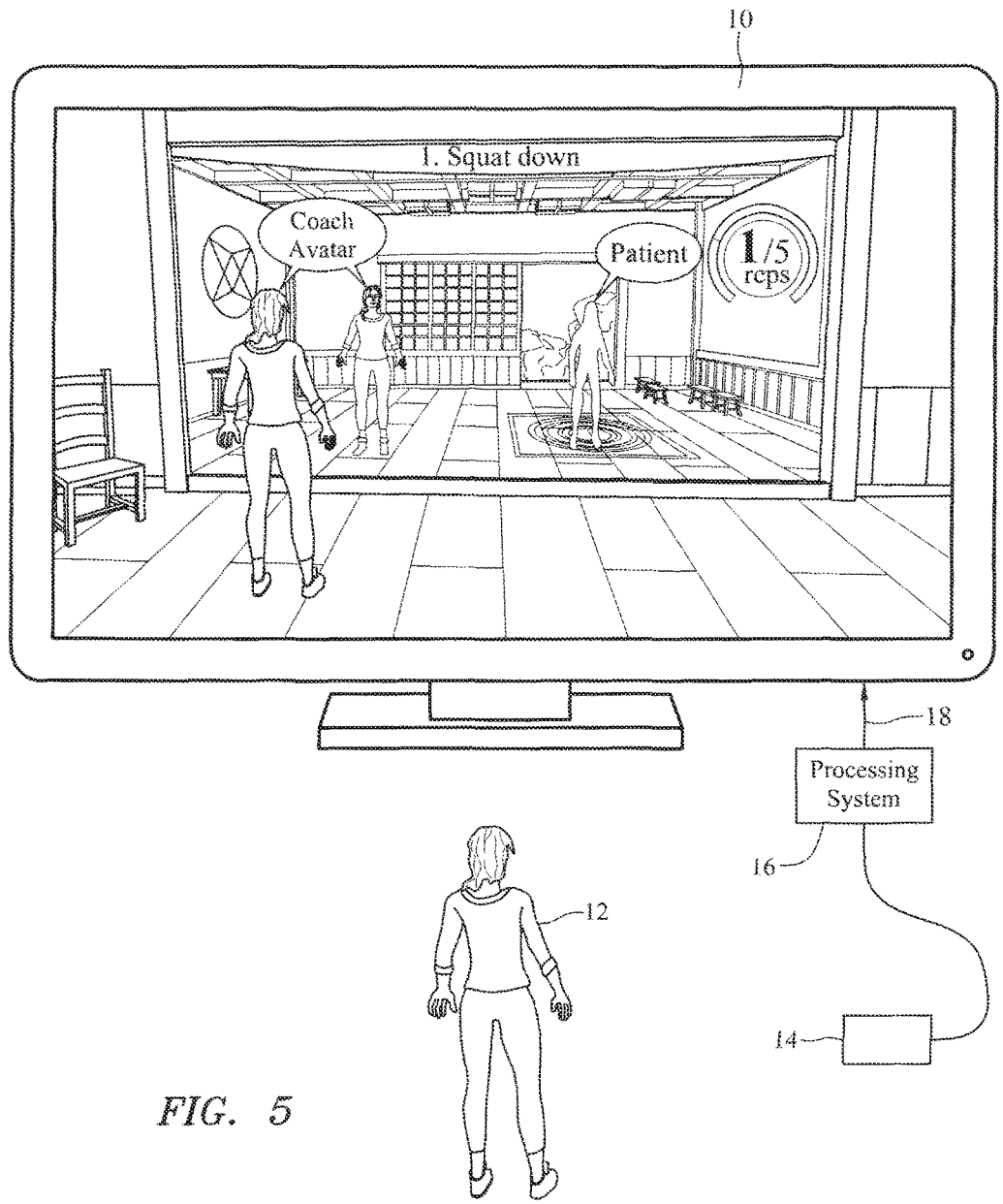
FIG. 5 shows the components of the overall system including the user position monitor and display.

FIG. 5 shows a perspective view of components of the overall system. A display device 10 is oriented toward a user 12 of the system. A user imaging unit is oriented toward the user 12. The user imaging system preferably is an imaging system capable of determining the spatial position of the user 12 in real time, preferably in color. One or more (multiple) user imaging systems may be utilized. The processing system 16 is coupled to the user imaging system(s) 14 to receive information relating to the user position and to compute the user positional information. The processing system 16 may be preferably comprised of computer hardware and software to perform the functions described herein. The processing system 16 compares the desired position as depicted by the first instructional image with the user positional information, such as to determine the differences between the two positions, such as to determine whether the user is complying with the desired action as shown by the first instructional image. The graphic to be rendered on the display device 10 is generated by the processing system 16, and coupled to the display device 10 via the output 18.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed:

1. A method for providing visual instruction to a user of a system, the system including a user imaging system and output adapted to couple to a display device to provide an output display to the user, including to guide user body motion, comprising the steps of:

receiving first user positional information from the user imaging system, generating a first mirror image of the user positional information utilizing the first user positional information from the user imaging system, generating a first instructional image having the same positional orientation as the first mirror image of the user positional information, and generating a composite output display including the first mirror image of the user positional information and the first instructional image, wherein the first mirror image and first instructional image are non-overlapping and wherein the first mirror image is the sole image of the user in the output display.

2. The method for providing visual instruction to a user of claim 1 further including a second instructional image in a mirror image orientation to the first instruction image.

3. The method for providing visual instruction to a user of claim 2 wherein the second instruction image depicts a different view of the first instruction image.

4. The method for providing visual instruction to a user of claim 3 wherein the different view comprises a back side view of the first Instructional image.

5. The method for providing visual instruction to a user of claim 1 wherein the first mirror image of the user positional information comprises an animated character.

6. The method for providing visual instruction to a user of claim 1 wherein the first mirror image of the user positional information comprises an avatar.

7. The method for providing visual instruction to a user of claim 1 wherein the first instructional image comprises an animated character.

8. The method for providing visual instruction to a user of claim 1 wherein the first instructional image comprises an avatar.

9. The method for providing visual instruction to a user of claim 1 wherein the first instructional image is provided in real time.

10. The method for providing visual instruction to a user of claim 1 wherein the user body motion includes limb motion.

11. The method for providing visual instruction to a user of claim 1 wherein the user body motion includes whole body motion.

12. The method for providing visual instruction to a user of claim 1 wherein the instruction comprises exercise instruction.

13. The method for providing visual instruction to a user of claim 1 wherein the instruction comprises rehabilitation instruction.

14. The method for providing visual instruction to a user of claim 1 wherein the imaging system includes a camera.

15. The method for providing visual instruction to a user of claim 14 wherein the camera is a color camera.

16. The method for providing visual instruction to a user of claim 14 wherein the camera is a depth camera.

17. The method for providing visual instruction to a user of claim 1 wherein the output display further includes textual annotation.

18. The method for providing visual instruction to a user of claim 17 wherein the textual annotation relates to the position of the instructional image.

19. The method for providing visual instruction to a user of claim 1 wherein an image is subject to dynamic state change.

20. The method for providing visual instruction to a user of claim 19 wherein the dynamic state change includes obscuring another image.

* * * * *